United States Patent [19]

Barrer

[11] 4,237,022

[45] Dec. 2, 1980

[54] TARTARIMIDES AND LUBRICANTS AND FUELS CONTAINING THE SAME

[75] Inventor: Daniel E. Barrer, Euclid, Ohio

[73] Assignee: The Lubrizol Corporation, Wickliffe, Ohio

[21] Appl. No.: 80,595

[22] Filed: Oct. 1, 1979

Related U.S. Application Data

[63] Continuation-in-part of Ser. No. 924,016, Jul. 12, 1978, abandoned.

[51] Int. Cl.$^3$ .......................... C10M 1/32; C01L 1/22; C07D 207/02
[52] U.S. Cl. .................................. 252/51.5 A; 44/63; 252/392; 260/326.5 FM
[58] Field of Search .............. 252/51.5 A, 392; 44/63; 260/326.5 FM

[56] References Cited

U.S. PATENT DOCUMENTS

| | | | |
|---|---|---|---|
| 2,811,429 | 10/1957 | Lappin et al. | 44/71 |
| 2,865,723 | 12/1958 | Lappin et al. | 44/71 |
| 2,977,309 | 3/1961 | Godfrey et al. | 252/51.5 A |
| 3,183,069 | 5/1965 | Udelhofen | 44/71 |
| 3,224,957 | 12/1965 | Kent | 44/71 X |
| 3,272,746 | 9/1966 | LeSuer et al. | 252/51.5 A |

*Primary Examiner*—W. J. Shine
*Attorney, Agent, or Firm*—Daniel N. Hall; William H. Pittman; Raymond F. Keller

[57] ABSTRACT

Tartarimides represented by the formula

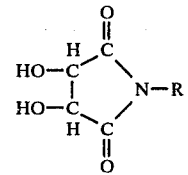

are disclosed, wherein R is a hydrocarbon-based radical having up to 150 carbon atoms. The disclosed tartarimides are useful as additives in lubricants and fuels.

39 Claims, No Drawings

TARTARIMIDES AND LUBRICANTS AND FUELS CONTAINING THE SAME

Cross-reference to Related Applications

This application is a continuation-in-part of copending U.S. application Ser. No. 924,016, filed July 12, 1978, now abandoned.

BACKGROUND OF THE INVENTION

1. Field of the Invention

The present invention is directed to new compositions of matter, and to normally liquid oleaginous composition containing the new compositions. More specifically, the present invention is concerned with a novel class of tartarimides produced by the reaction of tartaric acid and certain primary amines.

2. Description of the Prior Art

A number of carboxylic acids and/or their anhydrides, such as maleic and succinic acids, their derivatives such as amine salts, amides, amic acids, and esters prepared therefrom, have been well known as additives in lubricants and fuels for their corrosion and rust inhibiting properties. It was postulated generally that the substantial portion of the beneficial properties of such additives were derived from their acidic nature. Thus, dicarboxylic acids were reacted with fatty amines to produce the N-substituted amic acids (monoamides) as disclosed in U.S. Pat. No. 3,183,069. Similarly, $\alpha,\beta$-dicarboxylic acids were reacted with branched chain primary amines such as tertiary alkyl amines to produce the corresponding acidic reaction products for use as rust inhibitors in lubricants as disclosed in U.S. Pat. No. 2,977,309. The acidic reaction products of said 2,977,309 patent could be further reacted with long chain alcohols to prepare the corresponding ester products.

Amine salts of hydroxy aliphatic polycarboxylic acids have been prepared by the simple mixing of the amine with the acid either in the presence or absence of a solvent. Usually the amine is added in excess as disclosed in U.S. Pat. No. 2,811,429.

It is also well known that esters and acylated amines prepared from polycarboxylic acids and alcohols or amines are used as detergent or dispersant additives for lubricants and fuels. For a review of prior art patents concerned with such amine dispersants and detergents reference is made to U.S. Pat. No. 3,172,892; 3,184,474; 3,219,666; 3,272,746; 3,307,928; 3,331,776; 3,341,542; 3,346,354; and 3,381,022.

Inasmuch as the additives referred to hereinbefore and those described in the foregoing references have been of benefit as evidenced from their acceptance as commercial additives in lubricants and fuels, some problems still exist, particularly in fuels. It appears that products prepared from polyamines function best as dispersants in fuels such as gasoline, but tend to form aqueous emulsions with water, which give rise to harmful deposits in engines as well as rust problems.

The tartarimides of the present invention provide a new class of additive compounds having improved properties in terms of rust inhibition, fuel economy, and dispersancy. They also impart squeal and friction reductions to a variety of oleaginous compositions. For clarity, the term "oleaginous composition" refers to a normally liquid organic fluid composition comprising a major proportion of (1) a lubricating oil, (2) a fuel oil, (3) a distillate fuel, or (4) a synthetic oil.

In accordance with the foregoing, it is a principal object of the invention to provide new tartarimide compositions and use of same as novel additives to a broad class of oleaginous compositions. Another object of the invention is to provide ways and methods of preparing such new tartarimide additives, and their effective utilization as rust inhibitors, dispersants and demulsifiers in fuel compositions. A further object of the invention is to provide new tartarimide additives for use in lubricant fluids such as automatic transmission fluid and power steering fluid for effective reduction in squeal and friction as well as improvement of fuel economy. Other objects and advantages will become apparent from the following specification.

SUMMARY OF THE INVENTION

In one major aspect of the invention a new class of tartarimides is provided, said class being represented by the formula

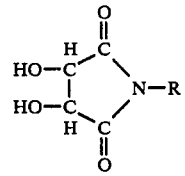

wherein R is a hydrocarbon-based radical of about 5 to about 150 carbon atoms or R'OR" in which R' is a divalent alkylene radical of 2 to 6 carbon atoms, and R" is a hydrocarbyl radical of about 5 to about 150 carbon atoms, or R.

DETAILED DESCRIPTION OF THE INVENTION

The tartarimides of the present invention are prepared by the reaction of tartaric acid and one or more primary amines, having the formula $RNH_2$ wherein R represents a hydrocarbon-based radical of about 5 to about 150 carbon atoms, or R'OR" in which R' is a divalent alkylene radical of 2 to 6 carbon atoms, R" is a hydrocarbyl radical of about 5 to about 150 carbon atoms, or R.

The hydrocarbon-based radicals of the present invention denote a radical having a carbon atom directly attached to the remainder of the molecule and having predominantly hydrocarbon character within the context of this invention. Such radicals include:

(1) hydrocarbyl radicals; that is aliphatic, (e.g., alkyl or alkenyl), alicyclic (e.g., cycloalkyl or cycloalkenyl), aromatic, aliphatic- and alicyclic-substituted aromatic, aromatic-substituted aliphatic and alicyclic radicals, and the like, as well as cyclic radicals wherein the ring is completed through another portion of the molecule (that is, any two indicated substituents may together form an alicyclic radical).

The hydrocarbyl radical is preferably aliphatic; e.g., alkyl or alkenyl of 5 or more carbon atoms. Examples include such monovalent alkyl radicals as pentyl, hexyl (caprylyl); capryl, lauryl, dodecyl, myristyl, pentadecyl, palmityl, margaryl, stearyl, and behenyl. Other alkenyl radicals include dodecenyl, myristoleyl, palmitoleyl, oleyl and linoleyl.

(2) Substituted hydrocarbon radicals, that is, radicals containing non-reactive or substantially non-hydrocarbon substituents which, in the context of this invention, do not alter the predominantly hydrocarbon character of the radical. Representative non-reactive or substantially non-reactive non-hydrocarbon or polar substituents which can be present as a substituent include halo substituents such as chloro, fluoro, bromo, and iodo; nitro; lower alkoxy such as butoxy and hexyloxy; lower alkylthio, such as methyl thio, pentyl thio and heptylthio. The substitution of and the nature of the substituent on the hydrocarbon-based radical is such that the essentially hydrocarbon character of the radical is not destroyed. Thus, in view of this requirement, these radicals normally have no more than two such polar or non-hydrocarbon substituents per substituted hydrocarbon radical and usually not more than one polar or non-hydrocarbon substituent for about every 10 carbon atoms in the substituted hydrocarbon radical. In other words, the substituted hydrocarbon radicals are analogous to the hydrocarbon groups discussed and exemplified above except for the presence of certain polar or non-hydrocarbon substituents which do not materially alter the predominantly hydrocarbon nature of the hydrocarbon-based radicals. The hydrocarbon-based radicals of the invention are substantially free from acetylenic unsaturation —C≡C—. Olefinic unsaturation, if present, usually averages to about one double bond per 8 carbon atoms.

As used in the present specification and claims, the term "lower", when used in conjunction with terminology designating a chemical group such as alkyl, alkenyl, alkylene and the like, is intended to describe such groups having a total carbon atom content of up to 7. For example "lower alkyl" includes all straight and branched chain alkyl groups of up to 7 carbon atoms.

Primary amines suitably preferred for the present invention are those represented by the formula $RNH_2$ wherein R represents a long hydrocarbyl radical of about 5 to about 150 carbon atoms, usually an alkyl radical of about 5 to about 50 carbons, preferably from 6 to 26 carbons and most preferably from 8 to 18 carbon atoms. Representative amines are those known as aliphatic fatty primary amines and commercially known as ARMEEN primary amines (products produced by Armor Chemicals, Chicago, Illinois). Typical fatty amines include alkyl amines such as n-hexylamine (caproylamine), n-octylamine (caprylylamine), n-decylamine (caprylamine), n-dodecylamine (laurylamine), n-tetradecylamine (myristylamine), n-pentadecylamine, n-hexadecylamine (palmitylamine), margarylamine, n-octadecylamine (stearylamine). These ARMEEN primary amines are available in both distilled and technical grades. While the distilled grade will provide a purer reaction product, the desirable tartarimide will form with reactions with the amines of technical grade.

Primary amines in which the hydrocarbon chain comprises olefinic unsaturation are also quite useful. Thus, the R hydrocarbyl radical may contain one or more olefinic unsaturation depending on the length of the chain, usually one double bond per 10 carbon atoms. The hydrocarbyl radical can contain up to 150 carbon atoms, normally about 50 carbons, preferably from 8 to 26 and most preferably from 12 to 18 carbon atoms. Representative amines are dodecenylamine, myristoleylamine, palmitoleylamine, oleylamine, and linoleylamine. Such unsaturated amines are also available under the ARMEEN name.

Other primary amines useful in the preparation of the tartarimides of the present invention are the primary ether amines $R''OR'NH_2$ wherein $R'$ is a divalent alkylene radical having 2 to 6 carbon atoms and $R''$ is a hydrocarbyl radical of about 5 to about 150 carbon atoms or having the same definition as the term R referred to earlier. These primary ether amines are generally prepared by the reaction of an alcohol $R''OH$ with an unsaturated nitrile. The $R''$ radical of the alcohol can be a hydrocarbon-based radical, as defined earlier, or an aliphatic-, or aromatic-based radical having up to about 150 carbon atoms. Typically, and for efficiency and economy, the alcohol is a linear or branched aliphatic alcohol with $R''$ having up to about 50 carbon atoms, preferably up to 26 carbon atoms and most preferably $R''$ has from 6 to 20 carbon atoms. The nitrile reactant can have from 2 to 6 carbon atoms with acrylonitrile being most preferred. Ether amines are known commercial products which are available under the name SUR-FAM$^{TM}$ produced and marketed by Worth Chemical Company, Worthington, Ohio 43085. Typical of such amines are those having from about 150 to about 400 molecular weights. Preferred etheramines are exemplified by those identified as SURFAM P14AB (branched $C_{14}$), SURFAM P16A (linear $C_{16}$), SURFAM P17AB (branched $C_{17}$). The carbon chain lengths (i.e., $C_{14}$, etc.) of the SURFAMS described above and used hereinafter are approximate and include the oxygen ether linkage. For example, a $C_{14}$ SURFAM would have the following general formula: $C_{10}$—O—$C_3$—$NH_2$.

The invention contemplates amines other than those described in detail herein as long as they satisfy the general criteria accorded hereinbefore to the formula $RNH_2$. It is essential for the primary amine to form the imide. Thus, primary amines of the formula

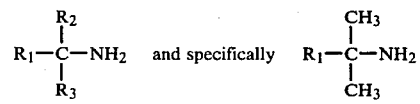

known commercially as Primene 81R-products of Rohm & Haas Co., Philadelphia, Pa.) are not contemplated by the present invention. It is believed that the foregoing amines are not capable of forming the corresponding tartarimides because of steric hindrance. Apparently, the branching at the carbon (tertiary) to which the amino radical is attached makes it difficult to form an adjacent cyclic imide.

The tartarimides of the present invention are prepared conveniently by reacting equimolar amounts of tartaric acid with the one or more of the corresponding primary amines. The tartaric acid used for preparing the tartarimides of the invention is the commercially available type (obtained from Sargent Welch), and it is likely to exist in one or more isomeric forms such as d-tartaric acid, l-tartaric acid or mesotartaric acid, often depending on the source (natural) or method of synthesis (from maleic acid). Of course, if desired, tartaric anhydride can be used in place of the tartaric acid in preparing the tartarimides of the present invention. The reaction is carried out at temperatures sufficiently high to form the imide. Thus, temperatures of about 110° to about 200° C., and preferably between about 120° to about 180° C., most preferably between about 130° to about 165° C. can be used. Lower temperatures normally take longer reaction times. The reaction is considered complete when two moles of water are removed per mole of tartaric acid and mole of the primary amine. The formation of the imide can be checked by known chemical techniques such as infrared or NMR spectra.

The foregoing reactions of preparing tartarimides of the invention are carried out conveniently in solvents, particularly those which can withstand relatively high reaction temperatures. Toluene is a very suitable solvent for this purpose as it allows convenient removal of water and it can be easily stripped by conventional techniques. Mineral oil can also be used as the solvent for the reaction in which case the oil may not have to be removed particularly when the formed tartarimides are destined as additives to lubricants. Other hydrocarbon solvents such as xylene, ethylbenzene, or even benzene may be used.

The tartarimides of the present invention can be solids, semi-solids, or oils depending on the particular primary amine used in preparing the tartarimide. For use as additives in oleaginous compositions including lubricating and fuel compositions the tartarimides will have to be soluble and/or stably dispersible in such oleaginous compositions. Thus, for example, compositions intended for use in oils are oil-soluble and/or stably dispersible in an oil in which they are to be used. The term "oil-soluble" as used in this specification and appended claims does not necessarily mean that all the compositions in question are miscible or soluble in all proportions in all oils. Rather, it is intended to mean that the composition is soluble in an oil (mineral, synthetic, etc.) in which it is intended to function to an extent which permits the solution to exhibit one or more of the desired properties. Similarly, it is not necessary that such "solutions" be true solutions in the strict physical or chemical sense. They may instead be micro-emulsions or colloidal dispersions which, for the purpose of this invention, exhibit properties sufficiently close to those of true solutions to be, for practical purposes, interchangeable with them within the context of this invention.

The term "stably dispersible in the normally liquid media" as used in this specification and appended clams is intended to mean a composition (e.g., a single tartarimide, a mixture of two or more tartarimides) is capable of being dispersed in a given medium to an extent which allows it to function in its intended manner. Thus, for example, where a composition of this invention is used in an oil, it is sufficient that the composition be capable of being suspended in the oil in an amount sufficient to enable the oil to possess one or more of the desired properties imparted to it by the suspended composition. Such suspension of the compositions can be achieved in various conventional ways. For example, in constantly circulating oil or oil in splash lubricating systems, physical agitation can keep the compositions suspended in oil. Likewise, conventional dispersants (such as the acylated nitrogen dispersants disclosed in U.S. Pat. No. 3,219,666) often found in lubricating oils and fuels promote the stable dispersion or suspension of the composition. In any event, the intended compositions will be "soluble" or "stably dispersible" in the normally liquid media in which they will be used in at least the minimum concentrations set forth elsewhere herein. Thus, the terminology "soluble" and "stably dispersible" is used in a conventional manner and will be understood to those of ordinary skill in the art.

The tartarimides of the invention can be combined with diluents to form a variety of concentrates; said diluents being substantially inert. As used in the specification and the appended claims, the term "substantially inert" when used to refer to reaction and storage equipment, solvents, diluents, and the like, is intended to mean that the solvent, diluent, etc., is inert to chemical or physical change under the conditions in which it is used so as not to materially interfere in an adverse manner with the preparation, storage, blending and/or functioning of the compositions, additive, compound, etc. of this invention in the context of its intended use. For example, small amounts of a solvent, diluent, etc. can undergo minimal reaction or degradation without preventing the making and using of the invention as described herein. In other words, such reaction or degradation, while technically discernible, would not be sufficient to deter the practical worker of ordinary skill in the art from making and using the invention for its intended purposes. "Substantially inert" as used herein is, thus, readily understood and appreciated by those of ordinary skill in the art.

As previously indicated, the tartarimide compositions of this invention are useful as additives for lubricants, in which they function primarily as rust and corrosion inhibitors, friction modifiers and demulsifiers. They can be employed in a variety of lubricants based on diverse oils of lubricating viscosity, including natural and synthetic lubricating oils and mixtures thereof. These lubricants include crankcase lubricating oils for spark-ignited and compression-ignited internal combustion engines, including automobile and truck engines, two-cycle engines, aviation piston engines, marine and railroad diesel engines, and the like. They can also be used in gas engines, stationary power engines and turbines and the like. Automatic transmission fluids, transaxle lubricants, gear lubricants, metal-working lubricants, hydraulic fluids and other lubricating oil and grease compositions can also benefit from the incorporation therein of the compositions of the present invention.

Natural oils include animal oils and vegetable oils (e.g., castor oil, lard oil) as well as liquid petroleum oils and solvent-treated or acid-treated mineral lubricating oils of the paraffinic, naphthenic or mixed paraffinic-naphthenic types. Oils of lubricating viscosity derived from coal or shale are also useful base oils. Synthetic lubricating oils include hydrocarbon oils and halo-substituted hydrocarbon oils such as polymerized and interpolymerized olefins (e.g., polybutylenes, polypropylenes, propylene-isobutylene copolymers, chlorinated polybutylenes, poly(1-hexenes), poly(1-octenes), poly(1-decenes), etc. and mixtures thereof]; alkylbenzenes (e.g., dodecylbenzenes, tetradecylbenzenes, dinonylbenzenes, di(2-ethylhexyl)benzenes, etc.); polyphenyls (e.g., biphenyls, terphenyls, alkylated polyphenyls, etc.), alkylated diphenyl ethers and alkylated diphenyl sulfides and the derivatives, analogs and homologs thereof and the like.

Alkylene oxide polymers and interpolymers and derivatives thereof where the terminal hydroxyl groups have been modified by esterification, etherification, etc. constitute another class of known synthetic lubricating oils. These are exemplified by the oils prepared through polymerization of ethylene oxide or propylene oxide, the alkyl and aryl ethers of these polyoxyalkylene polymers (e.g., methyl-polyisopropylene glycol ether having an average molecular weight of 1000, diphenyl ether of polyethylene glycol having a molecular weight of 500–1000, diethyl ether of polypropylene glycol having a molecular weight of 1000–1500, etc.) or mono- and polycarboxylic esters thereof, for example, the acetic acid esters, mixed $C_3$–$C_8$ fatty acid esters, or the $C_{13}$ Oxo acid diester of tetraethylene glycol.

Another suitable class of synthetic lubricating oils comprises the esters of dicarboxylic acids (e.g., phthalic acid, succinic acid, alkyl succinic acids and alkenyl succinic acids, maleic acid, azelaic acid, suberic acid, sebacic acid, fumaric acid, adipic acid, linoleic acid dimer, malonic acid, alkyl malonic acids, alkenyl malonic acids, etc.) with a variety of alcohols (e.g., butyl alcohol, hexyl alcohol, dodecyl alcohol, 2-ethylhexyl alcohol, ethylene glycol, diethylene glycol monoether, propylene glycol, etc.). Specific examples of these esters include dibutyl adipate, di(2-ethylhexyl) sebacate, di-n-hexyl fumarate, dioctyl sebacate, diisooctyl azelate, diisodecyl azelate, dioctyl phthalate, didecyl phthalate, dieicosyl sebacate, the 2-ethylhexyl diester of linoleic acid dimer, the complex ester formed by reacting one mole of sebacic acid with two moles of tetraethylene glycol and two moles of 2-ethyl-hexanoic acid, and the like.

Esters useful as synthetic oils also include those made from $C_5$ to $C_{12}$ monocarboxylic acids and polyols and polyol ethers such as neopentyl glycol, trimethylolpropane, pentaerythritol, dipentaerythritol, tripentaerythritol, etc.

Silicon-based oils such as the polyalkyl-, polyaryl-, polyalkoxy-, or polyaryloxy-siloxane oils and silicate oils comprise another useful class of synthetic lubricants (e.g., tetraethyl silicate, tetraisopropyl silicate, tetra-(2-ethylhexyl) silicate, tetra-(4-methyl-2-ethylhexyl) silicate, tetra-(p-tert-butylphenyl) silicate, hexa-(4-methyl-2-pentoxy)-disiloxane, poly(methyl)siloxanes, poly(methylphenyl)siloxanes, etc.). Other synthetic lubricating oils include liquid esters of phosphorus-containing acids (e.g., tricresyl phosphate, trioctyl phosphate, diethyl ester of decylphosphonic acid, etc.), polymeric tetrahydrofurans and the like.

Unrefined, refined and rerefined oils (and mixtures of each with each other) of the type disclosed hereinabove can be used in the lubricant compositions of the present invention. Unrefined oils are those obtained directly from a natural or synthetic source without further purification treatment. For example, a shale oil obtained directly from retorting operations, a petroleum oil obtained directly from distillation or ester oil obtained directly from an esterification process and used without further treatment would be an unrefined oil. Refined oils are similar to the unrefined oils except they have been further treated in one or more purification steps to improve one or more properties. Many such purification techniques are known to those of skill in the art such as solvent extraction, acid or base extraction, filtration, percolation, etc. Rerefined oils are obtained by processes similar to those used to obtain refined oils applied to refined oils which have been already used in service. Such rerefined oils are also known as reclaimed or reprocessed oils and often are additionally processed by techniques directed to removal of spent additives and oil breakdown products.

Generally, the lubricants of the present invention contain an amount of the composition of this invention sufficient to provide it with the aforementioned properties. Normaly this amount will be about 0.01 to about 5%, preferably about 0.1 to about 2.0% of the total weight of the lubricant. In lubricating oils operated under extremely adverse conditions, such as lubricating oils for marine diesel engines, the reaction products of this invention may be present in amounts of up to about 10% by weight.

The fuel compositions comprising the tartarimides of the present invention contain a major proportion of a normally liquid fuel, usually a hydrocarbonaceous petroleum distillate fuel such as aviation or motor gasoline as defined by ASTM Specification D-439-73 and diesel fuel or fuel oil as defined by ASTM Specification D-396. Normally liquid fuel compositions comprising non-hydrocarbonaceous materials such as alcohols, ethers, organo-nitro compounds and the like (e.g., methanol, ethanol, diethyl ether, methyl ethyl ether, nitromethane) are also within the scope of this invention as are liquid fuels derived from vegetable or mineral sources such as corn, alfafa, shale and coal. Normally liquid fuels which are mixtures of one or more hydrocarbonaceous fuels and one or more non-hydrocarbonaceous materials are also contemplated. Examples of such mixtures are combinations of gasoline and ethanol, diesel fuel and ether, and the like. Particularly preferred is gasoline, that is, a mixture of hydrocarbons having an ASTM boiling that is, a mixture of hydrocarbons having an ASTM boiling point of about 60° C. at the 10% distillation point to about 205° C. at the 90% distillation point.

Generally, these fuel compositions contain an amount of the tartarimides of this invention sufficient to impart sufficient rust inhibiting and demulsifying properties to the fuel; normally this amount is from about 1 to about 10,000; usually this amount is about 4 to about 200, preferably 10 to 100 parts by weight of the reaction product per million parts by weight of fuel. The preferred gasoline-based fuel compositions generaly exhibit excellent anti-rust properties, particularly under acidic and neutral conditions, and alkaline conditions up to pH 10. In addition, they exhibit excellent demulsifying properties thus not allowing the formation of harmful emulsions.

The fuel compositions of this invention can contain, in addition to the tartarimides of this invention, other additives which are well known to those of skill in the art. These can include anti-knock agents such as tetraalkyl lead compounds, lead scavengers such as haloalkanes (e.g., ethylene dichloride and ethylene dibromide), deposit preventors or modifiers such as triaryl phosphates, dyes, cetane improvers, antioxidants such as 2,6-di-tertiary-buty-4-methylphenyl, rust inhibitors, such as alkylated succinic acids and anhydrides, bacteriostatic agents, gum inhibitors, metal deactivators, demulsifiers, upper cylinder lubricants, anti-icing agents and the like.

In certain preferred fuel compositions of the present invention, the afore-described tartarimides are combined with an ashless dispersant in gasoline. Such ashless dispersants are preferably esters of a mono- or polyol and a high molecular weight mono- or polycarboxylic acid acylating agent containing at least 30 carbon atoms in the acyl moiety. Such esters are well known to those of skill in the art. See, for example, French Pat. No. 1,396,645, British Pat. Nos. 981,850 and 1,055,337 and U.S. Pat. Nos. 3,255,108; 3,311,558; 3,311,776; 3,346,354; 3,522,179; 3,579,450; 3,542,680; 3,381,022; 3,639,242; 3,697,428; 3,708,522; and British Patent Specification No. 1,306,529. These patents are expressly incorporated herein by reference for their disclosure of suitable esters and methods for their preparation. Generally, the weight ratio of the tartarimides of this invention to the aforesaid ashless dispersants is about 0.1 to about 10.0, preferably about 1 to about 10 parts of the tartarimides to 1 part ashless dispersant. In still another embodiment of this invention, the inventive additives are combined with Mannich condensation products formed from substituted phenols, aldehydes, polyamines, and substituted pyridines. Such condensation products are described in U.S. Pat. Nos. 3,649,659; 3,558,743; 3,539,633; 3,704,308; and 3,725,277.

The tartarimides of this invention can be added directly to the fuel or lubricant to form the fuel or lubricant compositions of this invention. Preferably, however, they are diluted with a substantially inert, normally liquid organic solvent/diluent such as mineral oil, xylene, or a normally liquid fuel as described above, to form an additive concentrate which is then added to the fuel or lubricant in sufficient amounts to form the inventive fuel or lubricant composition described herein. These concentrates generally contain about 10 to about 90% of the tartarimides of this invention and can contain in addition any of the abovedescribed conventional additives, particularly the aforedescribed ashless dispersants in the aforesaid proportions. The remainder of the concentrate is the solvent/diluent.

The invention also contemplates the use of other lubricant and/or fuel additives in combination with the tartarimides of this invention. Such other additives include, for example, auxiliary detergents and dispersants of the ash-producing or ashless type, corrosion- and oxidation-inhibiting agents, pour point depressing agents, extreme pressure agents, color stabilizers and anti-foam agents.

The ash-producing detergents are exemplified by oil-soluble neutral and basic salts of alkali or alkaline earth metals with sulfonic acids, carboxylic acids, or organic phosphorus acids characterized by at least one direct carbon-to-phosphorus linkage such as those prepared by the treatment of an olefin polymer (e.g., polyisobutene having a molecular weight of 1000) with a phosphorizing agent such as phosphorus trichloride, phosphorus heptasulfide, phosphorus pentasulfide, phosphorus trichloride and sulfur, white phosphorus and a sulfur halide, or phosphorothioic chloride. The most commonly used salts of such acids are those of sodium, potassium, lithium, calcium, magnesium, strontium and barium.

The term "basic salt" is used to designate metal salts wherein the metal is present in stoichiometrically larger amounts than the organic acid radical. The commonly employed methods for preparing the basic salts involve heating a mineral oil solution of an acid with a stoichiometric excess of a metal neutralizing agent such as the metal oxide, hydroxide, carbonate, bicarbonate, or sulfide at a temperature above 50° C. and filtering the resulting mass. The use of a "promoter" in the neutralization step to aid the incorporation of a large excess of metal likewise is known. Examples of compounds useful as the promoter include phenolic substances such as phenol, naphthol, alkylphenol, thiophenol, sulfurized alkylphenol, and condensation products of formaldehyde with a phenolic substance; alcohols such as methanol, 2-propanol, octyl alcohol, cellosolve, carbitol, ethylene glycol, stearyl alcohol, and cyclohexyl alcohol; and amines such as aniline, phenylenediamine, phenothiazine, phenyl-β-naphthylamine, and dodecylamine.

A particularly effective method for preparing the basic salts comprises mixing an acid with an excess of a basic alkaline earth metal neutralizing agent and at least one alcohol promoter, and carbonating the mixture at an elevated temperature such as 60°–200° C.

Auxiliary ashless detergents and dispersants are so called despite the fact that, depending on its constitution, the dispersant may upon combustion yield a non-volatile material such as boric oxide or phosphorus pentoxide; however, it does not ordinarily contain metal and therefore does not yield a metal-containing ash on combustion. Many types are known in the art, and any of them are suitable for use in the lubricants of this invention. The following are illustrative:

(1) Reaction products of carboxylic acids (or derivatives thereof) containing at least about 34 and preferably at least about 54 carbon atoms with nitrogen-containing compounds such as amine, organic hydroxy compounds such as phenols and alcohols, and/or basic inorganic materials. Examples of these "carboxylic dispersants" are described in British Pat. No. 1,306,529 and in many U.S. patents including the following:

| | | |
|---|---|---|
| 3,163,603 | 3,351,552 | 3,541,012 |
| 3,184,474 | 3,381,022 | 3,542,678 |
| 3,215,707 | 3,399,141 | 3,542,680 |
| 3,219,666 | 3,415,750 | 3,567,637 |
| 3,271,310 | 3,433,744 | 3,574,101 |
| 3,272,746 | 3,444,170 | 3,576,743 |
| 3,281,357 | 3,448,048 | 3,630,904 |
| 3,306,908 | 3,448,049 | 3,632,510 |
| 3,311,558 | 3,451,933 | 3,632,511 |
| 3,316,177 | 3,454,607 | 3,697,428 |
| 3,340,281 | 3,467,668 | 3,725,441 |
| 3,341,542 | 3,501,405 | Re 26,433 |
| 3,346,493 | 3,522,179 | |

(2) Reaction products of relatively high molecular weight aliphatic or alicyclic halides with amines, preferably polyalkylene polyamines. These may be characterized as "amine dispersants" and examples thereof are described for example, in the following U.S. patents:

| | |
|---|---|
| 3,275,554 | 3,454,555 |
| 3,438,757 | 3,565,804 |

(3) Reaction products of alkyl phenols in which the alkyl group contains at least about 30 carbon atoms with aldehydes (especially formaldehyde) and amines (especially polyalkylene polyamines), which may be characterized as "Mannich dispersants". The materials described in the following U.S. patents are illustrative:

| | |
|---|---|
| 3,413,347 | 3,725,480 |
| 3,697,574 | 3,726,882 |
| 3,725,277 | |

(4) Products obtained by post-treating the carboxylic, amine or Mannich dispersants with such reagents as urea, thiourea, carbon disulfide, aldehydes, ketones, carboxylic acids, hydrocarbon-substituted succinic anhydrides, nitriles, epoxides, boron compounds, phosphorus compounds or the like. Exemplary materials of this kind are described in the following U.S. patents:

| | | | |
|---|---|---|---|
| 3,036,003 | 3,282,955 | 3,493,520 | 3,639,242 |
| 3,087,936 | 3,312,619 | 3,502,677 | 3,649,229 |

| -continued | | | |
|---|---|---|---|
| 3,200,107 | 3,366,569 | 3,513,093 | 3,649,659 |
| 3,216,936 | 3,367,943 | 3,533,945 | 3,658,836 |
| 3,254,025 | 3,373,111 | 3,539,633 | 3,697,574 |
| 3,256,185 | 3,403,102 | 3,573,010 | 3,702,757 |
| 3,278,550 | 3,442,808 | 3,579,450 | 3,703,536 |
| 3,280,234 | 3,455,831 | 3,591,598 | 3,704,308 |
| 3,281,428 | 3,455,832 | 3,600,372 | 3,708,522 |

(5) Interpolymers of oil-solubilizing monomers such as decyl methacrylate, vinyl decyl ether and high molecular weight olefins with monomers containing polar substituents, e.g., aminoalkyl acrylates or acrylamides and poly-(oxyethylene)-substituted acrylates. These may be characterized as "polymeric dispersants" and examples thereof are disclosed in the following U.S. patents:

| | |
|---|---|
| 3,329,658 | 3,666,730 |
| 3,449,250 | 3,687,849 |
| 3,519,565 | 3,702,300 |

The above-noted patents are incorporated by reference herein for their disclosures of ashless dispersants.

Extreme pressure agents and corrosion- and oxidation-inhibiting agents are exemplified by chlorinated aliphatic hydrocarbons such as chlorinated wax; organic sulfides and polysulfides such as benzyl disulfide, bis(chlorobenzyl)disulfide, dibutyl tetrasulfide, sulfurized methyl ester of oleic acid, sulfurized alkylphenol, sulfurized dipentene, and sulfurized terpene; phosphosulfurized hydrocarbons such as the reaction product of a phosphorus sulfide with turpentine or methyl oleate; phosphorus esters including principally dihydrocarbon and trihydrocarbon phosphites such as dibutyl phosphite, diheptyl phosphite, dicyclohexyl phosphite, pentylphenyl phosphite, dipentylphenyl phosphite, tridecyl phosphite, distearyl phosphite, dimethyl naphthyl phosphite, oleyl 4-pentylphenyl phospite, polypropylene (molecular weight 500)-substituted phenyl phosphite, diisobutyl-substituted phenyl phosphite; metal thiocarbamates, such as zinc dioctyldithiocarbamate, and barium heptylphenyl dithiocarbamate; Group II metal phosphorodithioates such as zinc dicyclohexylphosphorodithioate, zinc dioctylphosphorodithioate, barium di(heptylphenyl)-phosphorodithioate, cadmium dinonylphosphorodithioate, and the zinc salt of a phosphorodithioic acid produced by the reaction of phosphorus pentasulfide with an equimolar mixture of isopropyl alcohol and n-hexyl alcohol.

The following examples are provided to further illustrate the invention. Unless otherwise indicated all temperatures are expressed in degrees Centigrade and all percentages and parts are percents and parts by weight.

EXAMPLE I

150 Parts of tartaric acid (obtained from Sargent Welch) is added to 173 parts of toluene and the mixture is heated with stirring to 100° C. 281 parts of Armeen O (essentially oleylamine, a product of Armak Chemicals, Chicago, Ill.) is added slowly and in small portions while the system is kept under nitrogen purge. After the addition of the Armeen O is completed the contents are heated to 130° C. at which temperature the water formed is removed by azeotroping, and collected. The temperature is then raised to 160° C., after no more water is collected and kept at about 160° C. for one hour under nitrogen purge to remove the toluene. The liquid residue is then filtered through diatomaceous earth to yield the desired N-oleyltartarimide. Analysis shows nitrogen content of 3.42% and hydroxyl content of 8.33%. The tartarimide can be expressed as

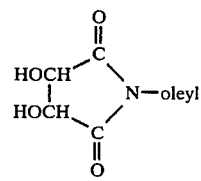

EXAMPLE II

Following the same procedure described in Example I 300 parts of tartaric acid are added to 519 parts of toluene and the mixture is heated with stirring to 90°–100° C. 370 parts of Armeen 12-D (distilled dodecylamine) are added slowly over about two hours. The temperature is raised to 110°–120° C. and the reaction is allowed to proceed for about 8 hours until no more water is observed. The reaction mixture is heated to 135° C. to strip the toluene (30 mm Hg). The mixture is cooled and a portion of 2-ethyl hexanol is added and followed by filtering through diatomaceous earth to yield the desired N-dodecyl-tartarimide.

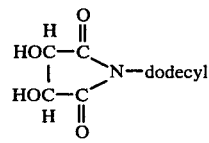

EXAMPLE IIA

The same procedure of Example II is followed except 300 parts of tartaric acid, 778 parts of toluene, and 370 parts of Armeen 12-D are used. To assist in stripping the toluene 450 parts of mineral oil SSU-100 are used in which oil the final N-dodecyl-tartarimide is soluble.

EXAMPLE III

The same procedure and amounts described in Example I is followed except the amine is substituted with 2-ethylhexylamine of which 258 parts are used. The reaction is conducted initially at 120° C. and then at 170° C. until all the water is removed (75 parts; theoretical 72 parts). The filtered solid product is soluble in oil. It can be represented by

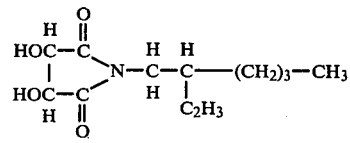

EXAMPLE IV

150 Parts of tartaric acid are added to 173 parts of toluene and the mixture is heated with stirring to 110° C. 130 parts representing half of the amount of dodecyl aniline is added to the heated mixture with nitrogen purge. The content including the amine is heated to 130° C. and held for about 5 hours. The second remaining half is added and the entire content is heated to 180°

C. azeotroping out both the formed water and toluene. The tartarimide residue is allowed to cool to yield brown solid at room temperature. The solid which is quite soluble in oil can be expressed as

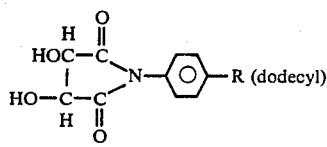

EXAMPLE V

150 Parts of tartaric acid is added to 2500 parts of an amino phenol represented by the formula

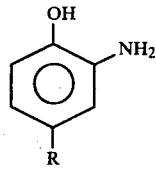

wherein R is a polybutenyl radical.
This amine has a molecular weight of about 2500. (The aminophenol used herein is prepared in accordance with the procedure described in German publication DT No. 2646241 published Apr. 28, 1977). The reaction between the acid and amine is carried out at 120° C. for 3 hours under nitrogen purge followed with additional heating at 160°–170° C. until no water is observed to form (39 parts collected). The imide product is then filtered warm through diatomaceous earth. The product is expressed as

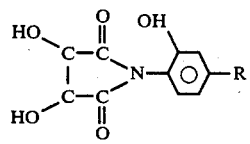

is soluble in oil.

EXAMPLE VI

Following the procedure described in Example I, 150 parts of tartaric acid are added to 173 parts of toluene and the mixture heated to 80° C. 258 Parts of SURFAM P17AB (Branched $C_{17}$ etheramine obtained from Worth Chemical, Worthington, Ohio) is added to the toluene-tartaric acid mixture and the entire contents are heated to 130° C. under nitrogen purge. The temperature is increased to 140° C. until the water is removed (32 parts collected). The toluene is stripped at 160° C. and the final imide product is filtered and collected. The oil-soluble tartarimide formed can be expressed as

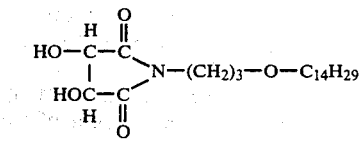

EXAMPLE VIA

The procedure of Example VI is followed except the following ether amines are used in place of the SURFAM P17AB:
1. SURFAM P24M (Linear $C_{12}$-$C_{14}$)
2. SURFAM P16A (Linear $C_{16}$)
3. SURFAM P18A (Linear $C_{18}$)
4. SURFAM P24A (Linear $C_{24\text{-}26}$)

EXAMPLE VII

Following the procedure of Example I, 246 parts of toluene, 150 parts of tartaric acid are used. The amine used is 171 parts of 2-ethylhexyl-3-aminopropylether (obtained from Union Carbide, New York, New York). The tartarimide product formed can be expressed as

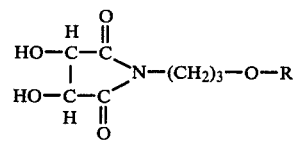

wherein R=2-ethylhexyl.

EXAMPLE VIII

150 Parts of tartaric acid, 173 parts of toluene and 215 parts of SURFAM P14AB (Branched $C_{14}$ etheramine obtained from Worth Chemical) are charged to a vessel and heated with stirring to 130° C. until no more water is observed to form. The reaction mass is then heated to 180° C. to remove all water (34 parts collected) and toluene. Complete stripping of the toluene is done at 20 mm Hg. The product is filtered through diatomaceous earth to yield a brown viscous mass. The formed imide which is soluble in oil can be represented as

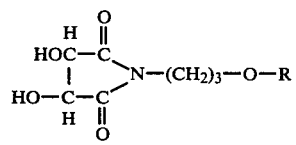

wherein R is a branched $C_{11}$ hydrocarbon.

EXAMPLE IX

A lubricating composition suitable for use as an automatic transmission fluid (ATF), is prepared using a mixture of mineral oils as the base oil, and as additives, by volume; 4.5% of a mixed-ester of a styrene-maleic anhydride copolymer reacted with a nitrogen-containing compound prepared as in U.S. Pat. No. 3,702,300; 0.58% of a zinc dithiophosphate; 0.80% of a calcium overbased petroleum sulfonate; 0.63% of the filtrate of Example 1; and 0.024% of a commercially available silicone-based antifoam agent.

The tartarimide additive functions primarily to improve friction properties of the above ATF composition.

EXAMPLE X

Several ATF compositions identical to the one described in Example IX are prepared with the following tartarimides:
(a) ATF+0.50% of the filtrate of Example II (b) ATF+0.30% of the filtrate of Example I+0.30% of the filtrate of Example II
(c) ATF+0.70% of the filtrate of Example VI
(d) ATF+0.75% of the filtrate of Example VIII.

The term ATF above refers to the automatic transmission fluid composition described in Example IX but without the tartarimide additives of the invention.

EXAMPLE XI

To a normally liquid hydrocarbon composition suitable for use as a fuel in an internal combustion engine is added the tartarimide of Example IX from a concentrate in a proportion of 9 pounds per thousand barrels. The treated gasoline is found to exhibit no rust under acidic, neutral and alkaline pH (up to pH 10) conditions. Moreover, the tartarimide provides desirable demulsifying properties in minimizing the formation of emulsions which give rise to harmful carburetor and engine deposits.

What is claimed is:

1. A composition of matter comprising one or more tartarimides represented by the formula

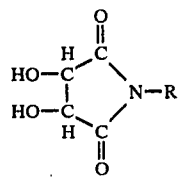

wherein R is an aliphatic-based or alicyclic-based radical of about 5 to about 150 carbon atoms or is R'OR" in which R' is a divalent alkylene radical of 2 to 6 carbon atoms, and R" is a hydrocarbyl radical of about 5 to about 150 carbon atoms, or R.

2. The composition of claim 1 wherein R is an aliphatic-based radical.

3. The composition of claim 2 wherein the aliphatic-based radical contains from about 5 to about 50 carbon atoms.

4. The composition of claim 3 wherein the aliphatic-based radical is an alkenyl radical having from about 8 to about 26 carbon atoms.

5. The composition of claim 4 wherein the alkenyl radical has from about 12 to about 18 carbon atoms.

6. The composition of claim 2 wherein the aliphatic-based radical is an alkyl radical having from about 5 to about 50 carbon atoms.

7. The composition of claim 6 wherein the alkyl radical has from about 6 to about 26 carbon atoms.

8. The composition of claim 7 wherein the alkyl radical has from about 8 to about 18 carbon atoms.

9. The composition of claim 5 wherein the alkenyl radical is selected from the group consisting of dodecenyl, myristoleyl, palmitoleyl, oleyl, and linoleyl radicals, and mixtures of two or more thereof.

10. The composition of claim 8 wherein the alkyl radical is selected from the group consisting of caprylyl, capryl, lauryl, myristyl, pentadecyl, palmityl, margaryl, and stearyl radicals, and mixtures of two or more thereof.

11. An oleaginous composition comprising a major proportion of a lubricating oil and a minor proportion of the tartarimide composition of claim 1.

12. An oleaginous composition comprising a major proportion of a lubricating oil and a minor proportion of the tartarimide composition of claim 2.

13. An oleaginous composition comprising a major proportion of a lubricating oil and a minor proportion of the tartarimide composition of claim 3.

14. An oleaginous composition comprising a major proportion of a lubricating oil and a minor proportion of the tartarimide composition of claim 4.

15. An oleaginous composition comprising a major proportion of a lubricating oil and a minor proportion of the tartarimide composition of claim 5.

16. An oleaginous composition comprising a major proportion of a lubricating oil and a minor proportion of the tartarimide composition of claim 6.

17. An oleaginous composition comprising a major proportion of a lubricating oil and a minor proportion of the tartarimide composition of claim 9.

18. An oleaginous composition comprising a major proportion of a lubricating oil and a minor proportion of the tartarimide composition of claim 7.

19. An oleaginous composition comprising a major proportion of a lubricating oil and a minor proportion of the tartarimide composition of claim 10.

20. An oleaginous composition comprising a major proportion of a normally liquid fuel and a minor proportion of the tartarimide composition of claim 1.

21. An oleaginous composition comprising a major proportion of a normally liquid fuel and a minor proportion of the tartarimide composition of claim 2.

22. An oleaginous composition comprising a major proportion of a normally liquid fuel and a minor proportion of the tartarimide composition of claim 3.

23. An oleaginous composition comprising a major proportion of a normally liquid fuel and a minor proportion of the tartarimide composition of claim 4.

24. An oleaginous composition comprising a major proportion of a normally liquid fuel and a minor proportion of the tartarimide composition of claim 5.

25. An oleaginous composition comprising a major proportion of a normally liquid fuel and a minor proportion of the tartarimide composition of claim 6.

26. An oleaginous composition comprising a major proportion of a normally liquid fuel and a minor proportion of the tartarimide composition of claim 9.

27. An oleaginous composition comprising a major proportion of a normally liquid fuel and a minor proportion of the tartarimide composition of claim 7.

28. An oleaginous composition comprising a major proportion of a normally liquid fuel and a minor proportion of the tartarimide composition of claim 10.

29. A concentrate comprising a normally liquid diluent and from 10 to 90% by weight of the tartarimide composition of claim 1.

30. A concentrate comprising a normally liquid diluent and from 10 to 90% by weight of the tartarimide composition of claim 2.

31. A concentrate comprising a normally liquid diluent and from 10 to 90% by weight of the tartarimide composition of claim 3.

32. A concentrate comprising a normally liquid diluent and from 10 to 90% by weight of the tartarimide composition of claim 4.

33. A concentrate comprising a normally liquid diluent and from 10 to 90% by weight of the tartarmide composition of claim 5.

34. A concentrate comprising a normally liquid diluent and from 10 to 90% by weight of the tartarimide composition of claim 6.

35. A concentrate comprising a normally liquid diluent and from 10 to 90% by weight of the tartarimide composition of claim 9.

36. A concentrate comprising a normally liquid diluent and from 10 to 90% by weight of the tartarimide composition of claim 7.

37. A concentrate comprising a normally liquid diluent and from 10 to 90% by weight of the tartarimide composition of claim 10.

38. A process for reducing squeal and/or friction in lubricating compositions used to lubricate power transmission means, which comprises incorporating into said lubricant compositions a minor effective amount of the tartarimide composition of claim 1.

39. A process for preparing an oleaginous composition having anti-corrosion and anti-rust properties, which comprises the steps of incorporating into said oleaginous composition a minor effective proportion of the tartarimide composition of claim 1.

* * * * *